(12) United States Patent
Købke

(10) Patent No.: US 12,233,000 B2
(45) Date of Patent: *Feb. 25, 2025

(54) METHOD AND A RECEPTACLE FOR EMPTYING A URINARY BAG

(71) Applicant: CURAS LTD., Bristol (GB)

(72) Inventor: Casper Lykkegaard Købke, Bristol (GB)

(73) Assignee: CURAS LTD., Bristol (GB)

(*) Notice: Subject to any disclaimer, the term of this patent is extended or adjusted under 35 U.S.C. 154(b) by 0 days.

This patent is subject to a terminal disclaimer.

(21) Appl. No.: 18/410,297

(22) Filed: Jan. 11, 2024

(65) Prior Publication Data
US 2024/0139021 A1 May 2, 2024

Related U.S. Application Data

(63) Continuation of application No. 18/091,643, filed on Dec. 30, 2022, now Pat. No. 11,896,513, which is a
(Continued)

(30) Foreign Application Priority Data

Sep. 14, 2016 (EP) ..................................... 16250014

(51) Int. Cl.
A61F 5/44 (2006.01)
A61F 5/451 (2006.01)

(52) U.S. Cl.
CPC .............. *A61F 5/4405* (2013.01); *A61F 5/44* (2013.01); *A61F 5/4401* (2013.01); *A61F 5/451* (2013.01)

(58) Field of Classification Search
CPC ........ A61F 5/4405; A61F 5/44; A61F 5/4401; A61F 5/451
See application file for complete search history.

(56) References Cited

U.S. PATENT DOCUMENTS 3,415,299 A * 12/1968 Hinman, Jr. .............. A61F 5/44
604/326
3,497,152 A 2/1970 Ivaldi
(Continued)

FOREIGN PATENT DOCUMENTS

WO 1997039705 10/1997
WO 2002045580 6/2002
(Continued)

OTHER PUBLICATIONS

International Search Report on corresponding PCT Application (PCT/IB2017/055548) from International Searching Authority (EPO) dated May 11, 2018.
(Continued)

*Primary Examiner* — Guy K Townsend
(74) *Attorney, Agent, or Firm* — Dinsmore & Shohl LLP

(57) ABSTRACT

A drainage bag system for urinary collection includes a urinary drainage bag having a first inlet and an inlet valve for regulating a flow of urine from a catheter into the urinary drainage bag via the first inlet, an outlet, and an outlet valve for regulating a flow of urine out of the urinary drainage bag. The drainage bag system further includes a receptacle bag of a foil or sheet material for emptying the urinary drainage bag and having a receptacle compartment for storing urine and a connector for providing a connection between the receptacle bag and the urinary drainage bag. The connector provides a second inlet constituting a receptacle inlet to the receptacle compartment when connected to the receptacle bag such that urine can flow into the receptacle compartment.

18 Claims, 9 Drawing Sheets

Related U.S. Application Data continuation of application No. 16/333,167, filed as application No. PCT/IB2017/055548 on Sep. 14, 2017, now Pat. No. 11,547,597.

(56) References Cited

U.S. PATENT DOCUMENTS

| | | | | |
|---|---|---|---|---|
| 3,661,143 A * | 5/1972 | Henkin | A61F 5/441 | 600/580 |
| 3,823,716 A * | 7/1974 | Hale | A61F 5/44 | 604/335 |
| 3,831,453 A * | 8/1974 | McWhorter | A61F 5/4404 | 604/323 |
| 3,965,910 A * | 6/1976 | Fischer | A61M 39/223 | 604/249 |
| 4,095,589 A * | 6/1978 | Manschot | A61B 10/007 | 600/580 |
| 4,306,705 A * | 12/1981 | Svensson | A61F 5/4405 | 604/905 |
| 4,417,892 A * | 11/1983 | Meisch | A61F 5/441 | 604/326 |
| 4,435,171 A * | 3/1984 | Goldberg | A61F 5/44 | 604/326 |
| 4,460,362 A * | 7/1984 | Bates | A61M 1/882 | 604/323 |
| 4,462,510 A * | 7/1984 | Steer | A61M 1/69 | 604/323 |
| 4,534,766 A * | 8/1985 | Steer | A61G 7/0503 | 604/350 |
| 4,620,846 A * | 11/1986 | Goldberg | A61M 1/285 | 604/28 |
| 4,634,437 A * | 1/1987 | Lowthian | A61F 5/44 | 600/580 |
| 4,702,740 A * | 10/1987 | Bates | A61M 1/882 | 604/323 |
| 4,723,950 A * | 2/1988 | Lee | A61M 1/882 | 604/326 |
| 4,909,478 A * | 3/1990 | Steer | F16K 5/0414 | 604/323 |
| 5,026,359 A * | 6/1991 | Burroughs | A61M 39/162 | 604/326 |
| 5,116,139 A * | 5/1992 | Young | A61J 19/00 | 383/65 |
| 5,211,642 A * | 5/1993 | Clendenning | A61M 1/70 | 604/326 |
| 5,331,689 A * | 7/1994 | Haq | A47K 11/12 | 604/326 |
| 5,460,606 A * | 10/1995 | Daneshvar | A61M 25/02 | 604/326 |
| 5,496,299 A * | 3/1996 | Felix | A61M 1/77 | 604/319 |
| 5,531,726 A | 7/1996 | Levesque | | |
| 5,616,138 A * | 4/1997 | Propp | A61F 5/451 | 604/350 |
| 5,902,294 A * | 5/1999 | Edwards | A61F 5/4405 | 604/350 |
| 5,919,146 A * | 7/1999 | Propp | A61B 5/208 | 604/326 |
| 6,132,407 A * | 10/2000 | Genese | A61F 5/4405 | 604/323 |
| 6,132,408 A * | 10/2000 | Lutz | A61F 5/4407 | 604/335 |
| 6,450,995 B1 * | 9/2002 | Prabhakar | A61F 13/84 | 604/385.101 |
| 6,482,190 B1 * | 11/2002 | Genese | A61F 5/4405 | 604/323 |
| 6,503,208 B1 * | 1/2003 | Skovlund | A61B 5/205 | 600/561 |
| 6,543,064 B1 * | 4/2003 | Prall | A61G 9/006 | 4/144.1 |
| 6,682,503 B1 * | 1/2004 | Fariss | F16K 15/147 | 604/326 |
| 6,709,420 B1 * | 3/2004 | Lincoln | B67D 3/041 | 604/323 |
| 6,793,651 B1 * | 9/2004 | Bennett | A61F 5/4405 | 604/328 |
| 7,008,407 B1 * | 3/2006 | Kamp | A61F 5/4405 | 604/327 |
| 7,462,171 B2 * | 12/2008 | Salvadori | A61F 5/4404 | 604/327 |
| 7,833,169 B2 * | 11/2010 | Hannon | A61B 10/007 | 604/327 |
| 8,092,436 B2 * | 1/2012 | Christensen | A61M 1/69 | 73/290 R |
| 8,177,772 B2 * | 5/2012 | Christensen | A61M 39/26 | 604/536 |
| 8,292,858 B2 * | 10/2012 | Burgess | A61F 5/4405 | 604/326 |
| 8,337,475 B2 * | 12/2012 | Christensen | A61M 1/80 | 604/317 |
| 8,790,320 B2 * | 7/2014 | Christensen | A61J 1/22 | 604/318 |
| 9,669,205 B2 * | 6/2017 | Jin | A61F 5/4405 | |
| 9,821,105 B2 * | 11/2017 | Yeh | A61M 1/159 | |
| 10,507,318 B2 * | 12/2019 | Jin | A61M 39/26 | |
| 10,576,262 B2 * | 3/2020 | Tsai | A61J 1/10 | |
| 11,187,364 B2 * | 11/2021 | Jin | F16L 37/32 | |
| 11,547,597 B2 * | 1/2023 | Kobke | A61F 5/4405 | |
| 2002/0091364 A1 * | 7/2002 | Prabhakar | A61F 5/451 | 604/327 |
| 2009/0010975 A1 * | 1/2009 | Shiraishi | A23P 20/00 | 424/443 |
| 2009/0030379 A1 * | 1/2009 | Burgess | A61M 39/22 | 604/249 |
| 2009/0209926 A1 * | 8/2009 | Cochran | A61F 5/4404 | 604/332 |
| 2012/0066825 A1 * | 3/2012 | Birbara | A47K 11/12 | 4/309 |
| 2013/0226118 A1 * | 8/2013 | Enriquez | A61F 5/453 | 604/347 |
| 2014/0213934 A1 * | 7/2014 | Ellis | A61B 10/0096 | 600/573 |
| 2014/0276216 A1 * | 9/2014 | Lipinsky | A61B 10/007 | 600/573 |
| 2015/0059901 A1 * | 3/2015 | Jin | A61F 5/4405 | 137/798 |
| 2015/0190272 A1 * | 7/2015 | Chang | A61F 5/445 | 604/335 |
| 2016/0302960 A1 * | 10/2016 | Schertiger | A61F 5/451 | |
| 2016/0339227 A1 * | 11/2016 | Tsai | A61M 39/1011 | |
| 2017/0252549 A1 * | 9/2017 | Jin | F16L 37/32 | |
| 2019/0231582 A1 * | 8/2019 | Kobke | A61F 5/44 | |
| 2019/0357837 A1 * | 11/2019 | Lyu | A61B 5/205 | |
| 2020/0164196 A1 * | 5/2020 | Jin | A61F 5/4405 | |
| 2022/0090720 A1 * | 3/2022 | Jin | A61F 5/4405 | |
| 2023/0143263 A1 * | 5/2023 | Kobke | A61F 5/4401 | 604/328 |

FOREIGN PATENT DOCUMENTS

| | | |
|---|---|---|
| WO | 2002094128 | 11/2002 |
| WO | 2006110695 | 10/2006 |
| WO | 2009010975 | 1/2009 |
| WO | 2015068270 | 5/2015 |
| WO | 2016008493 | 1/2016 |

OTHER PUBLICATIONS

Written Opinion on corresponding PCT Application (PCT/IB2017/055548) from International Searching Authority (EPO) dated May 11, 2018.

* cited by examiner

METHOD AND A RECEPTACLE FOR EMPTYING A URINARY BAG

CROSS-REFERENCE TO RELATED APPLICATIONS

This application is a continuation of U.S. patent application Ser. No. 18/091,643, filed on Dec. 30, 2022, which is a continuation of U.S. patent application Ser. No. 16/333,167, filed on Mar. 13, 2019, issued as U.S. Pat. No. 11,547,597, which is a National Phase entry, under 35 U.S.C. Section 371 (c), of International Application No. PCT/IB2017/055548, filed Sep. 14, 2017, claiming priority from European Patent Application No. 16250014.4, filed Sep. 14, 2016. The disclosures of the prior US Application and the International Application are incorporated herein by reference in their entirety.

FEDERALLY SPONSORED RESEARCH OR DEVELOPMENT

Not Applicable

BACKGROUND

The present invention relates to a method and a receptacle bag for emptying a urinary drainage bag and a drainage bag system for urinary collection.

In urinary catheterization, a latex, polyurethane, or silicone tube known as a urinary catheter is inserted into a patient's bladder via the urethra, or via suprapubic catheterization. Alternatively, the catheterization may also take place with placement of a urisheath (condom type catheter). Catheterization allows the patient's urine to drain freely from the bladder for collection, measuring of volume, monitoring, and analysis. In a closed urinary drainage system, the catheter extends to a urinary drainage bag where its end is coupled to an inlet of a collecting compartment of the urinary drainage bag for collecting the urine in the collecting compartment of the urinary drainage bag.

The urinary drainage bag can typically hold between 0.5 liter to 5 liters of urine. When the urinary drainage bag is full, or emptied for other reasons, it is in a first alternative example replaced by a new and empty urinary drainage bag by removing the catheter from the inlet of the filled urinary drainage bag and placing the catheter on an inlet of the new urinary drainage bag.

In a second alternative example the urinary drainage bag comprises an outlet through which urine in the compartment of the urinary drainage bag can flow out of. An outlet valve regulates flow of urine out through the outlet. In the second alternative example the urinary drainage bag is emptied by having the outlet valve in an open state. In the second alternative example urine can also be taken from the urinary drainage bag for testing, for measuring of volume and analysis.

Examples of catheter systems and urinary drainage bags are described in the below patent applications and patents to which reference is made and which are hereby incorporated in the present application by reference. The references comprise: WO16008493, WO15067270, WO06110695, U.S. Pat. Nos. 5,116,139, 5,531,726 WO02094128, U.S. Pat. No. 3,497,152, and WO9739705.

SUMMARY

The emptying of the urinary drainage bag is a non-sterile process and it is an object of the present invention to improve the emptying of the urinary drainage bag such that the emptying becomes more hygienic and safe for the nursing staff and patients with less risk of infection. It is a second object of the present invention that the emptying becomes sterile. It is also an object of the object of the present invention to dispense of the collected urine in the urinary drainage bag via waste handling methods. It is a further object of the present invention to shield and protect the urine drainage bags' outlet, which is important for overall hygiene reasons.

The above object and advantages together with numerous other objects and advantages, which will be evident from the description of the present invention, are according to a first aspect of the present invention obtained by:

A drainage bag system for urinary collection comprising:
  a urinary drainage bag comprising a first inlet and an inlet valve for regulating a flow of urine from a catheter into said urinary drainage bag via said first inlet, an outlet and an outlet valve for regulating a flow of urine out of said urinary drainage bag; and
  a receptacle bag of a foil or sheet material for emptying said urinary drainage bag comprising a receptacle compartment for storing urine, and a connector for providing a connection between said receptacle bag and said urinary drainage bag, said connector providing a second inlet constituting a receptacle inlet to said receptacle compartment when connected to said receptacle bag such that urine can flow into said receptacle compartment.

The receptacle bag may be made from a first foil and a second foil being welded together, i.e., placing the first foil on top of the other and welding them together. The welding is placed proximate the edges of the foils, which means that the welding is between 0-15 mm from the edges. The foils may be thin polyethylene foils having a thickness between 0.01-0.2 mm. The welded foils have an inner side constituting a side of the receptacle compartment and an outer side facing away from the receptacle bag.

The foils may have a flat rectangular shape. The first foil may comprise a number of foil layers and the second foil may comprise a number of foil layers.

The receptacle bag may be formed by stretch blow moulding a preform. The preform may be formed in an injection moulding process. In the stretch blow moulding process, the preform is heated above its glass transition temperature and blown, using high pressure air, such that a container part is expanded. The expanded container part constitutes the receptacle compartment. The preform comprises the connector for connection to the urine drainage bag. The preform may be made from polyethylene.

The receptacle bag may be made from a fibrous pulp material by forming two paperboard sheets, which may be glued together. An alternative material for the receptacle bag could be other organic based materials. The receptacle bag can also be formed through the use of a vacuum forming process.

The receptacle bag may comprise a receptacle valve for regulating the flow of urine into the receptacle compartment via the receptacle inlet. When the receptacle valve is in an open state, fluid can flow into the receptacle compartment through the passageway and when the receptacle valve is in a closed state, the passageway is blocked and fluid is prevented from flowing out of the receptacle compartment.

The receptacle valve may be a non-return valve for allowing fluid to flow in only one direction, the direction being into the receptacle compartment. Fluid pressure from the receptacle valve side facing the receptacle compartment results in the receptacle valve closing and fluid pressure from the opposite side results in the receptacle valve opening. When the urinary drainage bag is placed higher than the receptacle bag, gravity alone may act on the urine in the urinary drainage bag causing the urine to flow out of the urinary drainage bag and putting pressure on the receptacle valve such that the receptacle valve opens where after the urine flows further down into the receptacle compartment.

The receptacle compartment is a pouch or a pocket forming an enclosed space for storing urine emptied from the urine drainage bag comprising a volume between 0.5 liter to 5 liter. The receptacle compartment may have a larger volume than the urinary drainage bag. A small urinary drainage bag with respect to a receptacle bag may be emptied a number of times into the receptacle bag. For example, a one liter urinary drainage bag may be emptied five times into a five liter receptacle bag before the receptacle bag is brought to waste handling. Alternatively, the receptacle bag may extend the overall capacity of the system such that a receptacle bag of five liter and a urinary drainage bag of five liter provides for a system with a capacity of five liter in total.

The connector may comprise a flexible and firm material such as silicone, PVC or PVC-free alternative materials, etc. The connector may be manufactured separate from the receptacle bag and attached to the receptacle bag by nursing staff, or it may be attached to the receptacle bag during manufacturing of the receptacle bag.

The connector may be formed as a longitudinal tube. The connector may be manufactured separate from the receptacle bag and attached to the receptacle bag by nursing staff, or it may be attached to the receptacle bag during manufacturing of the receptacle bag.

Alternatively, the connector may be formed in a two-shot molding process, wherein two separate materials are incorporated into one part. A first part of the connector may be made from a first material for coupling to the receptacle bag and a second part of the connector may be made from a second material for coupling to the outlet. The second material is preferably softer than the first material.

A proximal end of the connector with respect to the receptacle bag may be formed as a female funnel. A female funnel has an increasing circumference or radius as the funnel comes towards its end. A distal end of the connector may be formed as a female funnel. The distal end of the connector goes around the outlet tube. The shape of the distal end of the connector may complement or counterpart the shape of the outlet tube such that the distal end can engage the outlet tube.

The distal end may be placed around the outlet or the outlet valve of the urinary drainage bag soon after a patient has been fitted with a closed urinary drainage system and even before any urine has been collected in the urinary drainage bag. In this way the connector may shield the outlet or the outlet valve of the urinary drainage bag and protect against drainage or infection up though the outlet or the outlet valve. The distal end of the connector may provide tension with respect to the outlet or the outlet valve. The distal end of the connector may stretch around the outlet.

The outlet of the urinary drainage bag may project from the urinary drainage bag in the form of an outlet tube. The outlet tube has an outlet passageway for fluid communication between a proximal end and a distal end of the outlet tube with respect to a collecting compartment of the urinary drainage bag such that fluid can flow out of the collecting compartment. The distal end of the outlet tube may have a conical shape or a male funnel shape.

The flow of fluid through the outlet passageway is regulated by the outlet valve of the urinary drainage bag. When the outlet valve is in an open state fluid can flow out of the urinary drainage bag through the outlet passageway and when the outlet valve is in a closed state the outlet passageway is blocked and fluid is prevented from flowing out of the urinary drainage bag. The outlet valve may be operated manually between the open state and the closed state. The outlet valve may be a cross valve. The cross valve comprises a stem and a gate. A handle can be actuated for moving the gate from a closed position to an open position and vice versa. In an alternative solution the cross valve of the urinary drainage bag is substituted by a pull-push opening or another valve type, such as a finger flip or leaver tap. Theses valve type would likewise be possible to insert into the female funnel of the receptacle bag.

According to a further embodiment, a fluid absorbent powder is placed in the receptacle compartment by filling it through a pipe down through the receptacle valve before the connector is coupled to the outlet, i.e., before the receptacle bag is interconnected with the urinary drainage bag. In this way the receptacle bag can be produced as a finished entity with the receptacle valve where after the fluid absorbent powder can be placed in the receptacle compartment after the receptacle bag has been produced, in the form of lose powder or a long sleeve/pouch. The receptacle bag may comprise the pipe for passing the fluid absorbent powder through the first inlet and into the receptacle compartment. The receptacle valve prevents the fluid absorbent powder to come out of the receptacle bag again.

In an embodiment the fluid absorbent powder is a super absorbent polymer or slush powder, which are polymers that can absorb and retain large amounts of a liquid relative to their own mass. It is likewise possible to use an organic material having similar properties.

The fluid absorbent powder may also be provided in a sachet that that dissolve when it comes into contact with a liquid.

The fluid absorbent powder reacts with the urine when the powder and the urine meet in the receptacle compartment. The reaction results in a gel or a substance with a higher viscosity than the viscosity of the urine. In an embodiment the fluid absorbent powder absorb aqueous solutions such as urine through hydrogen bonding with water molecules.

The fluid absorbent powder stabilizes the urine that has been emptied from the urinary drainage bag and filled into the receptacle compartment of the receptacle bag. The receptacle bag may then be transported to a waste handling facility or to further processing of the patients collected urine output.

The receptacle compartment may contain urine comprising cancer drug. In an embodiment the receptacle bag comprises a barrier around the receptacle compartment for reducing radiation from cancer drug in the urine waste.

According to a further embodiment, the receptacle bag comprises a hanger for hanging the receptacle bag on the urinary drainage bag by placing it at a lower height than a height of the urinary drainage bag.

The hanger may be a lanyard or a cord or a string. As the outlet valve is opened gravity may force the urine from the urinary drainage bag down into the receptacle bag. As the urinary drainage bag is emptied and the receptacle bag is filled the nursing staff does not have to support the increasing weight of the receptacle bag.

The hanger may provide tension between the receptacle bag and the urinary drainage bag such that the connector is less likely to fall off.

The receptacle bag is provided with one or more holes such as two, three or four holes. The one or more holes are located along a first side of the receptacle bag corresponding to a side comprising the receptacle inlet. The hanger extends through the holes and may form a ring or have two ends that can be tied together for forming a closed ring.

The hanger may comprise a handle for holding the receptacle bag with such that nursing staff can carry the receptacle bag from bedside to waste handling point thereby not having to touch the receptacle bag.

In an embodiment the hanger comprises a tie-knot for adjusting the length of the hanger. A width of the hanger is between 2 mm-6 mm for twisting the hanger and adjusting the length via the twisting.

According to a further embodiment the hanger is supported by the outlet valve. The hanger may be tied to the outlet valve or placed around the outlet valve. This provides for a simple procedure for the nursing staff to attach the receptacle bag to the urinary drainage bag, especially in embodiments where the outlet valve comprises a cross valve.

According to a further embodiment the connector is removed from the outlet and a closure is placed on the connector for closing a passageway into the receptacle compartment. This provides added safety from drainage during transport of a filled receptacle bag. The closure may be a plug or spigot that fits tightly in the passageway. The closure may be a separate entity or attached to the receptacle bag. In an embodiment the closure is attached to the hanger or to a lanyard or string attached to the receptacle bag.

In an embodiment the receptacle bag may comprise a first tube coupled to the receptacle inlet. The first tube is coupled or connected to the receptacle inlet and projects from the receptacle bag. The first tube has a first conduit for fluid communication between a proximal end and a distal end of the first tube such that fluid can flow through the first tube and into the passageway of the receptacle inlet. The distal end of the first tube may have a conical shape or a male funnel shape. A male funnel has a decreasing circumference or radius as the funnel comes towards its end. The connector may be coupled to the first tube at a proximate end of the connector.

According to a second aspect of the present invention the above objects and advantages are obtained by:

A method for emptying a urinary drainage bag, comprising the steps of:
  providing a urinary drainage bag comprising a first inlet and an inlet valve for regulating a flow of urine from a catheter into said urinary drainage bag via said first inlet, said urinary drainage bag further comprising an outlet and an outlet valve for regulating a flow of urine out of said urinary drainage bag;
  providing a receptacle bag of a foil or sheet material for emptying said urinary drainage bag comprising a receptacle compartment for storing urine, and a connector for providing a connection between said receptacle bag and said urinary drainage bag, said connector providing a second inlet constituting a receptacle inlet to said receptacle compartment when connected to said receptacle bag such that urine can flow into said receptacle compartment; and
  connecting said connector to said outlet and opening said outlet valve for providing a flow of urine out of said urinary drainage bag and into said receptacle bag.

According to a third aspect of the present invention the above objects and advantages are obtained by:

A receptacle bag of a foil or sheet material for emptying a urinary drainage bag, comprising a receptacle compartment for storing urine emptied from the urinary drainage bag, and a connector for providing a connection between said receptacle bag and said urinary drainage bag, said connector providing a second inlet constituting a receptacle inlet to said receptacle compartment when connected to said receptacle bag such that urine can flow into said receptacle compartment.

According to a fourth aspect of the present invention the above objects and advantages are obtained by:

A drainage system for wound drainage comprising:
  a receptacle bag (26) of a foil or sheet material for collecting liquid from said wound, and a polymer tube between said wound and said receptacle bag, said receptacle bag encompassing a receptacle compartment (28) for storing said liquid, a receptacle inlet into said receptacle compartment, said receptacle inlet constituted by a connector having a distal end with respect to said receptacle compartment, said distal end defining a female funnel for receiving said polymer tube, said polymer tube having a first tube end, and a second tube end, said polymer tube extending with a length of more than 0.5 m between said first tube end, and said second tube end, said first tube end defining a male funnel placed in said female funnel, said second tube end comprising a male Luer lock fitting.

The invention will be explained in more detail below in connection with advantageous embodiments of the invention with reference to the drawings.

DETAILED DESCRIPTION

Figure 1:
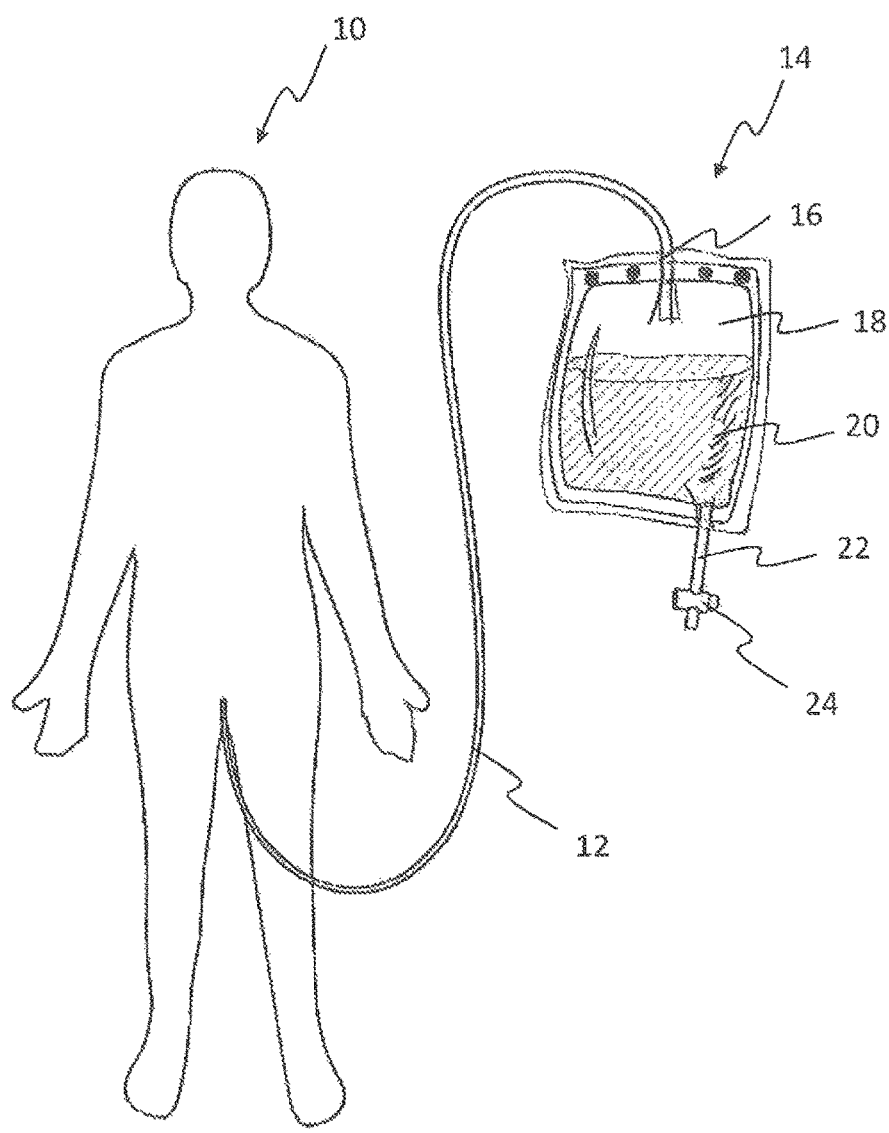
FIG. 1 shows the principal of a traditional closed urinary drainage connected to the patient.

The present invention will now be described more fully hereinafter with reference to the accompanying drawings, in which exemplary embodiments of the invention are shown. The invention may, however, be embodied in different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout. Like elements will, thus, not be described in detail with respect to the description of each figure.

Figure 3:
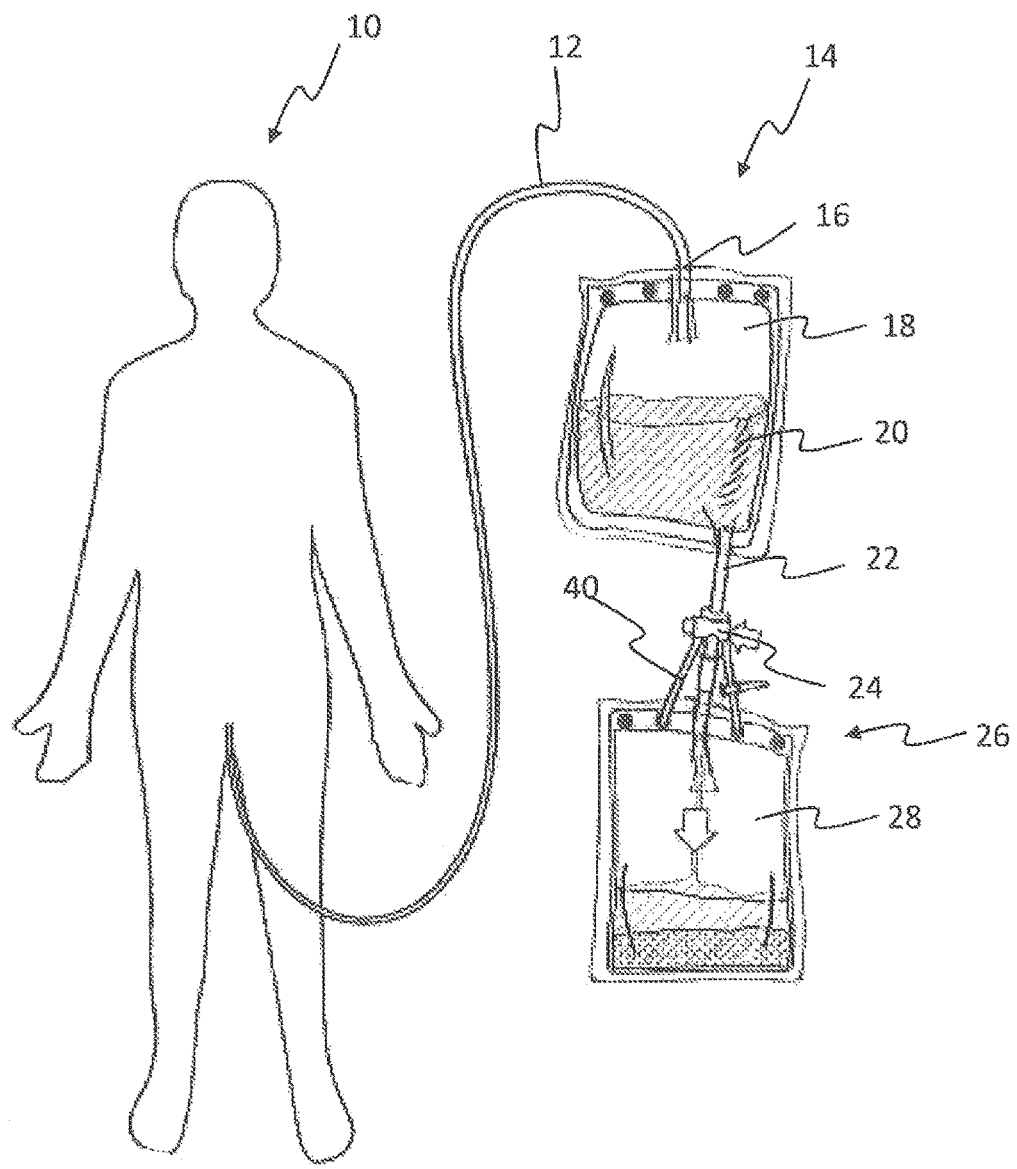
FIG. 3 is a perspective view of a receptacle bag connected to a urinary drainage bag.
Figure 4:
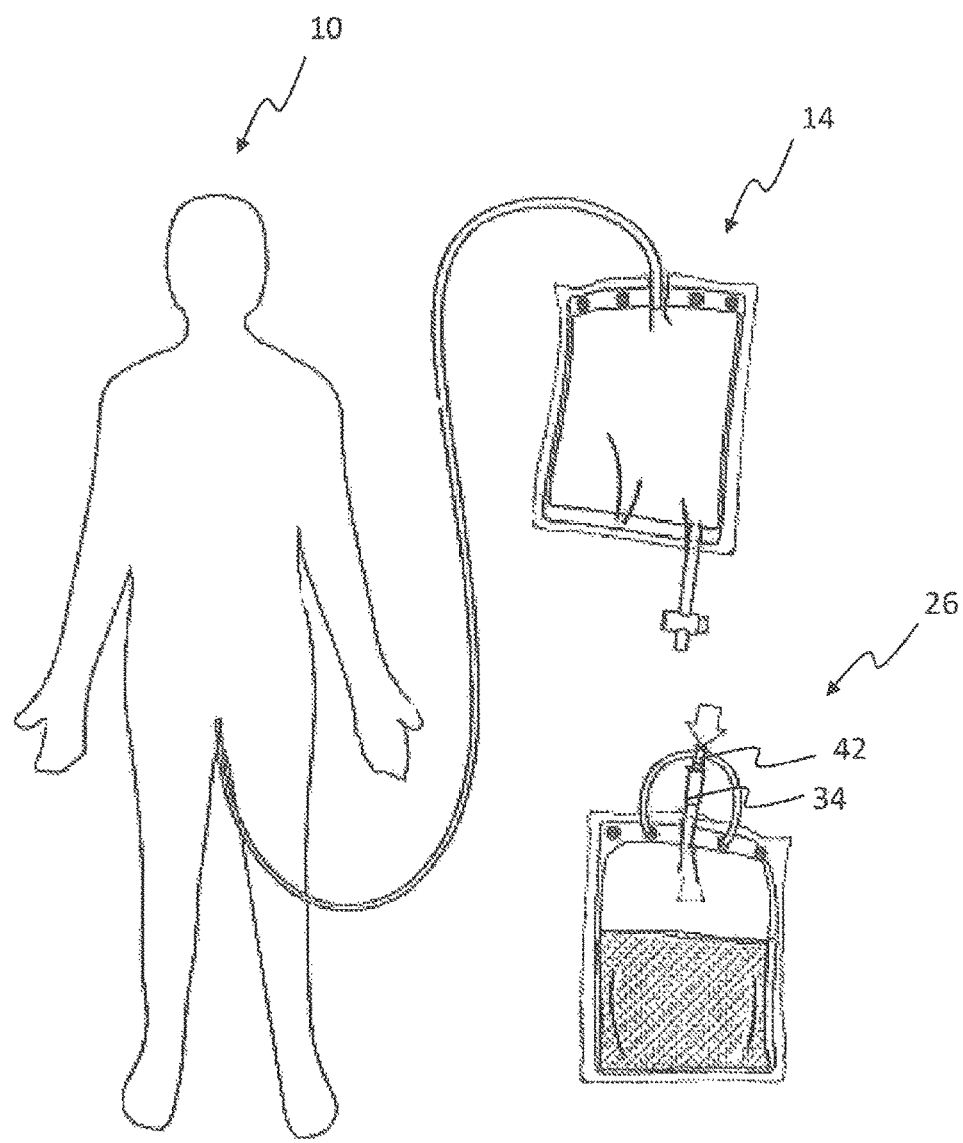
FIG. 4 is a perspective view of a closed urinary drainage and a receptacle bag after the contents of the urinary drainage bag have been transferred to the receptacle bag.

FIG. 1 shows a traditional closed urinary drainage connected to a patient 10. A catheter 12 extends to a urinary drainage bag 14 where its end is coupled to a first inlet 16 to a collecting compartment 18 of the urinary drainage bag 14 for collecting urine 20 in the collecting compartment 18 of the urinary drainage bag 14. It should be noted that the dimension and position of the urinary drainage bag 14 in FIGS. 1, 3, and 4 are not actually proportions of the urinary drainage bag 14 or receptacle bag 26, but are used for the purpose of showing in which context the invention is used.

The collecting compartment 18 is a pouch or a pocket forming an enclosed space for collecting urine comprising a volume between 0.5 liter to 5 liters.

The outlet 22 of the urinary drainage bag 14 projects from the urinary drainage bag 14 in the form of an outlet tube. The outlet tube has an outlet passageway for fluid communication between a proximal end and a distal end of the outlet tube with respect to a collecting compartment 18 of the urinary drainage bag 14 such that fluid can flow out of the collecting compartment. The distal end of the outlet tube has a conical shape (male funnel shape).

The flow of fluid through the outlet passageway is regulated by the outlet valve 24. When the outlet valve 24 is in an open state fluid can flow out of the urinary drainage bag 14 through the outlet passageway and when the outlet valve 24 is in a closed state the outlet passageway is blocked and fluid is prevented from flowing out of the urinary drainage bag 14. The outlet valve 24 may be operated manually between the open state and the closed state. The outlet valve 24 may be a cross valve. The cross valve comprises a stem and a gate. A handle can be actuated for moving the gate from a closed position to an open position and vice versa.

Figure 2:
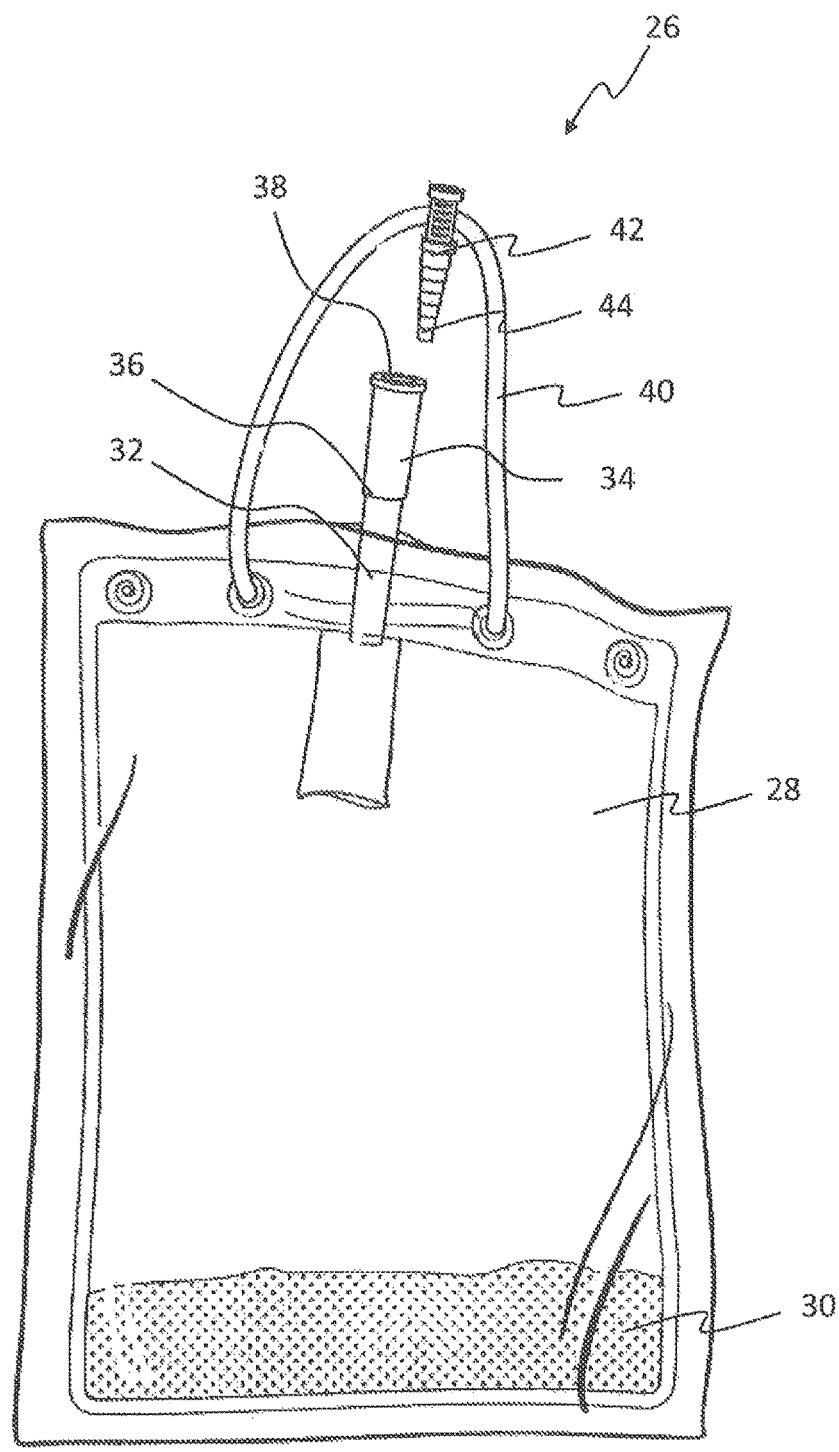
FIG. 2 is a perspective view of an embodiment of a receptacle bag for emptying a urinary drainage bag.

FIG. 2 is a perspective view of an example of a receptacle bag 26 for emptying the urinary drainage bag 14. In the example shown in FIG. 2 the receptacle bag 26 has been made by welding two rectangular PE foils together. The foils are welded together 0.2 mm to 1 cm from the edge of the foils.

In the top of the receptacle bag a first tube 32 has been welded on in order to provide for a passageway into a receptacle compartment 28 for storing urine emptied from the urinary drainage bag 14.

The receptacle compartment 28 comprises a fluid absorbent powder 30 for stabilizing urine. The fluid absorbent powder was placed in the receptacle bag 26 via a pipe.

The receptacle bag 26 comprises a receptacle valve (not shown) for regulating a flow of urine from the urinary drainage bag into the receptacle compartment 28.

The receptacle bag 26 was made with a hanger 40 for hanging the receptacle bag 26 on the urinary drainage bag 14. The hanger 40 is a lanyard. A closure 42 for closing a passageway into the receptacle bag was attached to the hanger 40. The closure comprises a closure end 44 in the form of a plug, which has a conical shape and is tapered.

A connector 34 is coupled to the receptacle inlet via a first tube 32. The connector 34 comprises a first end 36 for engaging with the first tube 32 and a second end 38 for engaging with an outlet 22 or an outlet valve 24 of the urinary drainage bag 14. The first end 36 comprises a female funnel for placement around the first tube 32. The second end 38 comprises a female funnel for placement around the outlet 22 or the outlet valve 24 of the urinary drainage bag.

In another example the connector 34 and the first tube 32 are made as an integral unit in one piece that can be coupled to the receptacle bag in a welding process. The connector 34 provides a passageway into the receptacle compartment. The connector 34 extends from the receptacle bag 26 and has a free end in the shape of a female funnel at the second end 38.

FIG. 3 is a perspective view of the receptacle bag 26 connected to the urinary drainage bag 14. The outlet valve 24 is set to an open state such that urine can flow from the collecting receptacle compartment 18 of the urinary drainage bag 14 through the outlet 22 and into the receptacle compartment 28 of the receptacle bag 26. As the urine flows into the receptacle compartment 28 it reacts with the fluid absorbent powder 30. The reaction results in a gel or a substance with a higher viscosity than the viscosity of the urine.

The hanger 40 is a lanyard or a cord or a string. As the outlet valve 24 is opened gravity may force the urine from the urinary drainage bag 14 down into the receptacle compartment 28 of the receptacle bag 26. As the urinary drainage bag 14 is emptied and the receptacle compartment 28 is filled the nursing staff does not have to support the increasing weight of the receptacle bag.

The receptacle bag 26 is provided with one or more holes such as two, three or four holes. The one or more holes are located along a first side of the receptacle bag corresponding to a side comprising the receptacle inlet. The lanyard extends through the holes and may form a ring or have two ends that can be tied together for forming a closed ring.

The lanyard comprises a tie-knot for adjusting the length of the lanyard. A width of the lanyard is between 2 mm-6 mm for twisting the lanyard and adjusting the length via the twisting. The lanyard is placed around the outlet valve. The outlet valve is a cross valve.

The distal end of the connector is placed around the distal end of the outlet tube such that urine from the drainage bag may be funneled into the receptacle bag. This reduces the risk of spillage from where the outlet tube and the connector overlap each other. This would be the case where a separate adapter is used to interconnect the drainage bag and the receptacle bag. The system comprising the drainage bag and the receptacle bag consist of one single overlap of interconnected tubes, i.e., the connector is integral with the receptacle bag, and it is placed directly over the outlet tube of the drainage bag, and there are no adapters.

FIG. 4 is a perspective view of the closed urinary drainage and the receptacle bag 26 after the content of the urinary drainage bag 14 have been emptied into the receptacle bag 26.

The closure 42 is placed the connector 34 for closing a passageway in the connector 34 and to provide added safety from drainage during transport of a filled receptacle bag.

The closure 42 is a plug having a conical shape that fits tightly in the passageway of the connector 34.

Figure 5:
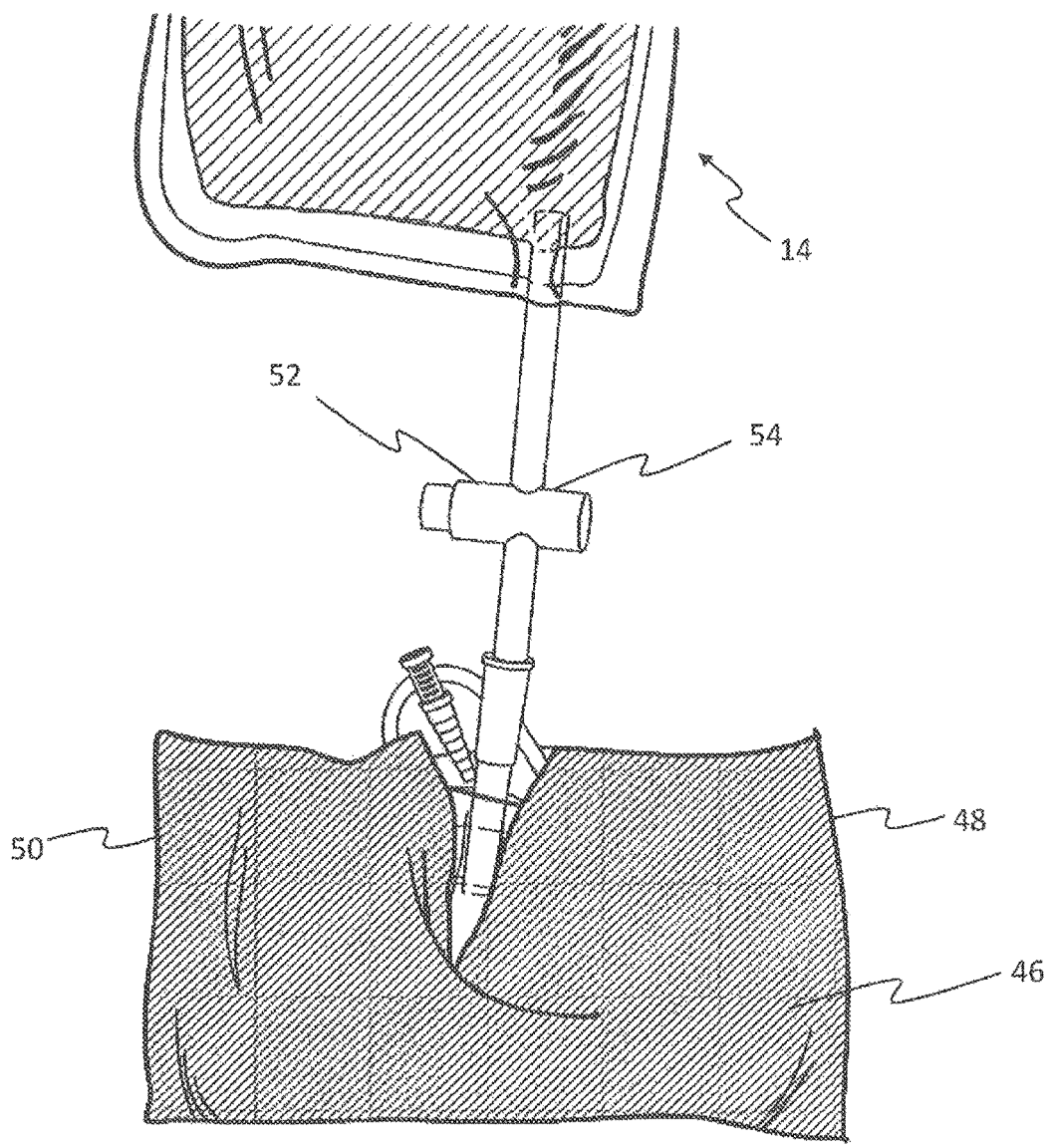
FIG. 5 is a perspective view of a receptacle bag in its packaging wherein the packaging is partly opened to allow the receptacle bag to be connected with a urinary drainage bag.

FIG. 5 is a perspective view of a receptacle bag 26 in its packaging 46 wherein the packaging 46 is partly opened to allow the connector 34 to extend out of the packaging and be connected with the urinary drainage bag 14. The packaging comprises a mark for indicating a part of the packaging to be opened. The mark is located between a first side 48 and a second side 50. The first side 48 being opposite the second side 50. The difference between the distance from the mark to the first side 48 and the distance from the mark to the second side 50 is less than 20%. The receptacle bag 26 is placed in the packaging 46 with connector 34 located between the first side 48 and the second side 50 and closer to the mark than to the first side 48 or the second side 50.

The urinary drainage bag 14 comprises a cross valve which together with the outlet tube from the urinary drainage bag has a cross shaped cross section. The cross valve comprises a first arm 52 and a second arm 54. The first arm extends a first distance from the outlet tube and the second arm extends a second distance from the outlet tube. The first distance and the second distance are at least 0.5 cm.

Figure 6:
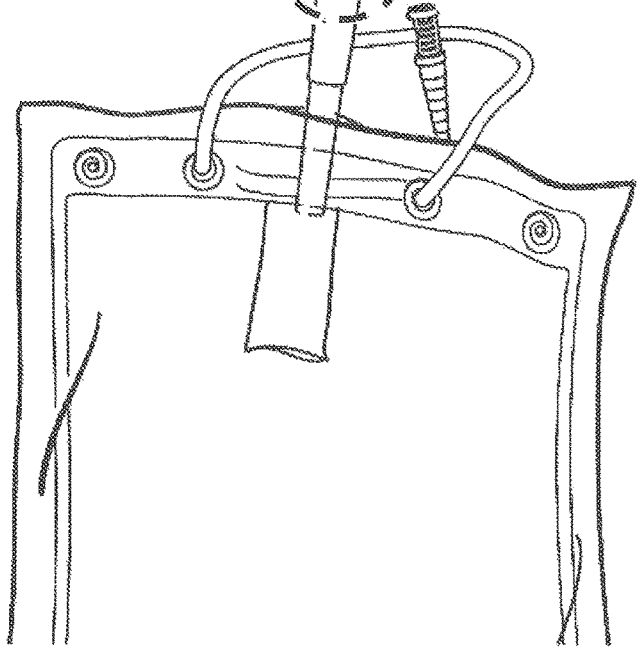
FIG. 6 is a perspective view of an embodiment of a receptacle bag.

FIG. 6 is a perspective view of an example of a receptacle bag 26 for emptying the urinary drainage bag 14. A distal end of the outlet tube with respect to the urinary drainage bag comprises a female part 56 of a bayonet coupling for coupling with a male part 58 on the second end 38 of the connector 34. The section of FIG. 6 surrounded by a dashed circle is shown as an enlarged section in FIG. 7. In an alternative embodiment (not shown), the male part is formed inside the second end of the connector 34 allowing the second outlet 22 of the urinary drainage bag to be inserted into the connector 34 of receptacle bag 26, whereby the second outlet 22 is rotated, e.g., 45 degrees, for obtaining a connection between the receptacle bag 26 and the urinary drainage bag 14.

Figure 7:
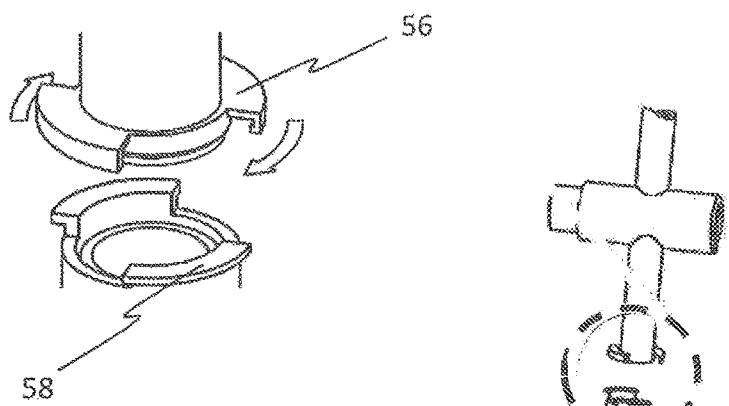
FIG. 7 is a perspective view of an enlarged section of an embodiment of a receptacle bag.

FIG. 7 is a perspective view of an enlarged section of the section encircled by a dashed circle in FIG. 6. The enlarged section shows female part 56 of a bayonet coupling for coupling with a male part 58 on the second end 38 of the connector 34.

Figure 8:
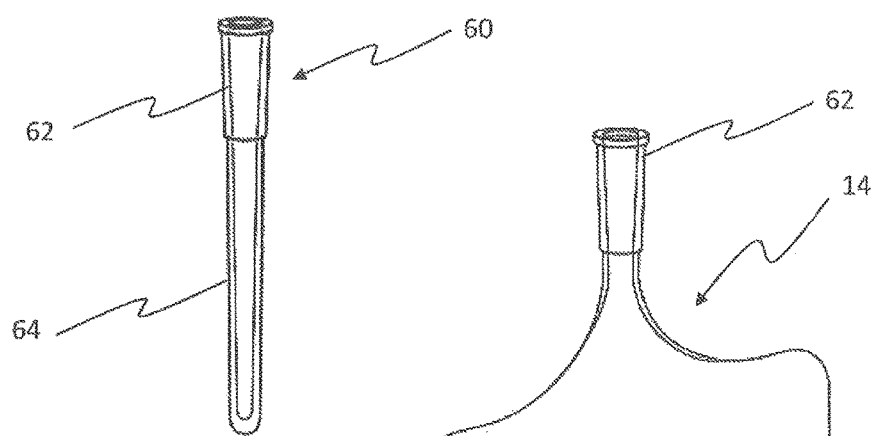
FIG. 8 is a perspective view of an embodiment of a preform of a receptacle bag.

FIG. 8 is a perspective view of an example of a preform 60 of a receptacle bag to be produced in a stretch blow moulding process. The preform comprises a container part 64 and a neck 62. The preform 60 is formed in an injection moulding process. In the stretch blow moulding process the preform is heated above its glass transition temperature and blown, using high pressure air, such that the container part is expanded. The neck 62 comprises the connector 34 for connection to a urine drainage bag. It should be noted that a non-return valve is not shown in FIG. 8-11.

Figure 9:
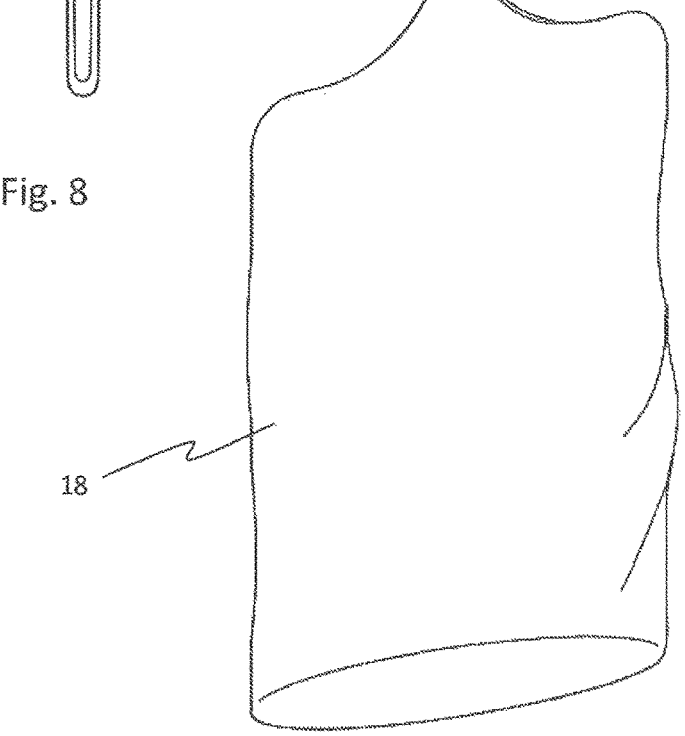
FIG. 9 is a perspective view of an embodiment of a receptacle bag.

FIG. 9 is a perspective view of an example of a receptacle bag 26 that has been produced in a stretch blow moulding process. The receptacle bag 26 comprises a neck 62 and a receptacle compartment 18. The neck 62 comprises the connector 34 for connection to a urine drainage bag.

Figures 10, 11:
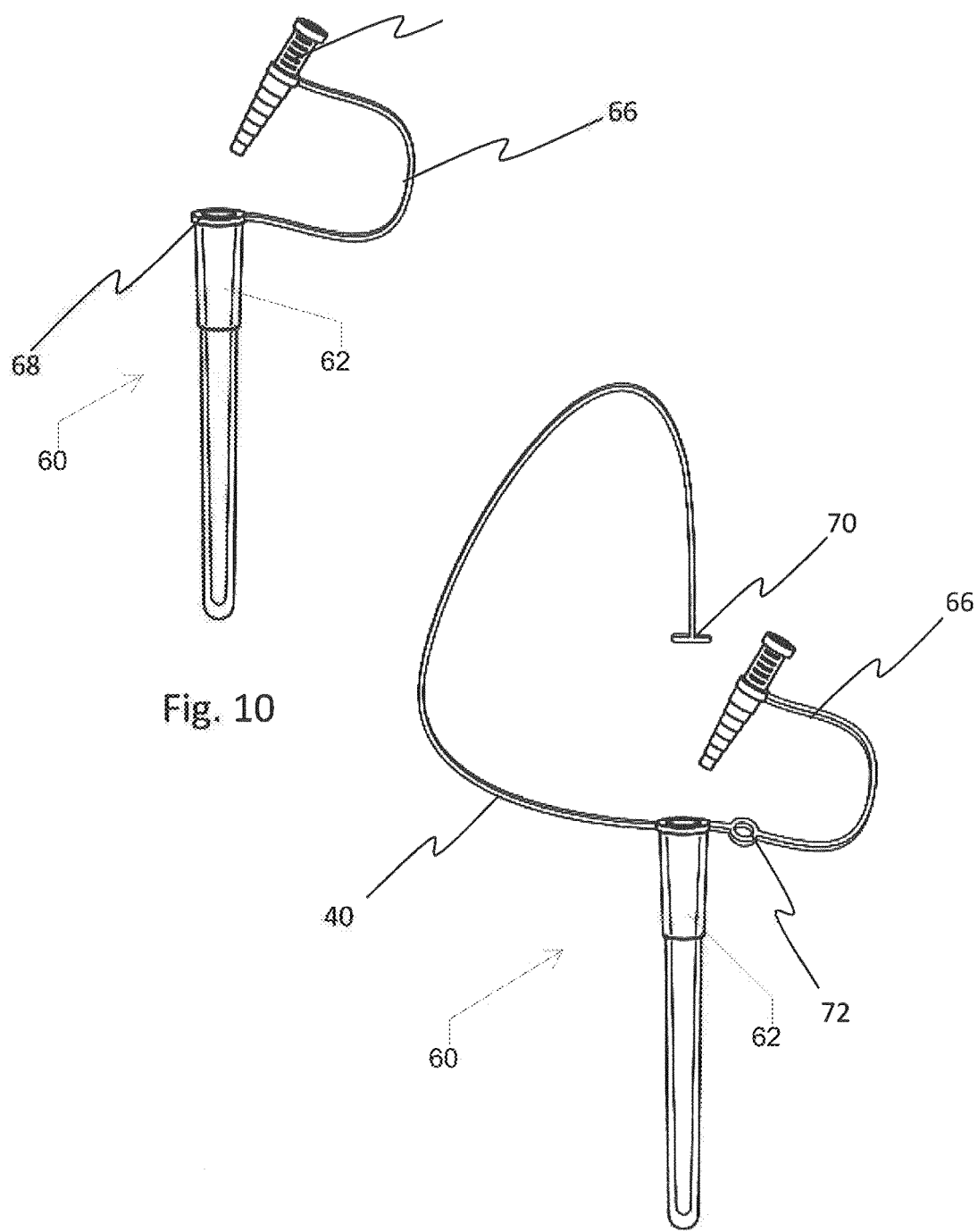
FIG. 10 is a perspective view of an embodiment of a preform of a receptacle bag.
FIG. 11 is a perspective view of an embodiment of a preform of a receptacle bag.

FIG. 10 is a perspective view of an example of a preform 60 of a receptacle bag to be produced in a stretch blow moulding process. The preform 60 comprises a closure 42 at distal end of a tether 66. The tether comprises a loop 68 at a proximal end of the neck 62 for placement around the neck 62 of the preform 60.

FIG. 11 is a perspective view of an example of a preform 60 of a receptacle bag to be produced in a stretch blow moulding process. The preform comprises a tether 66 and a hanger 40. The tether comprises a loop 72. A distal end 70 of the hanger 40 comprises an anchor for placement in the loop 72.

Figure 12:
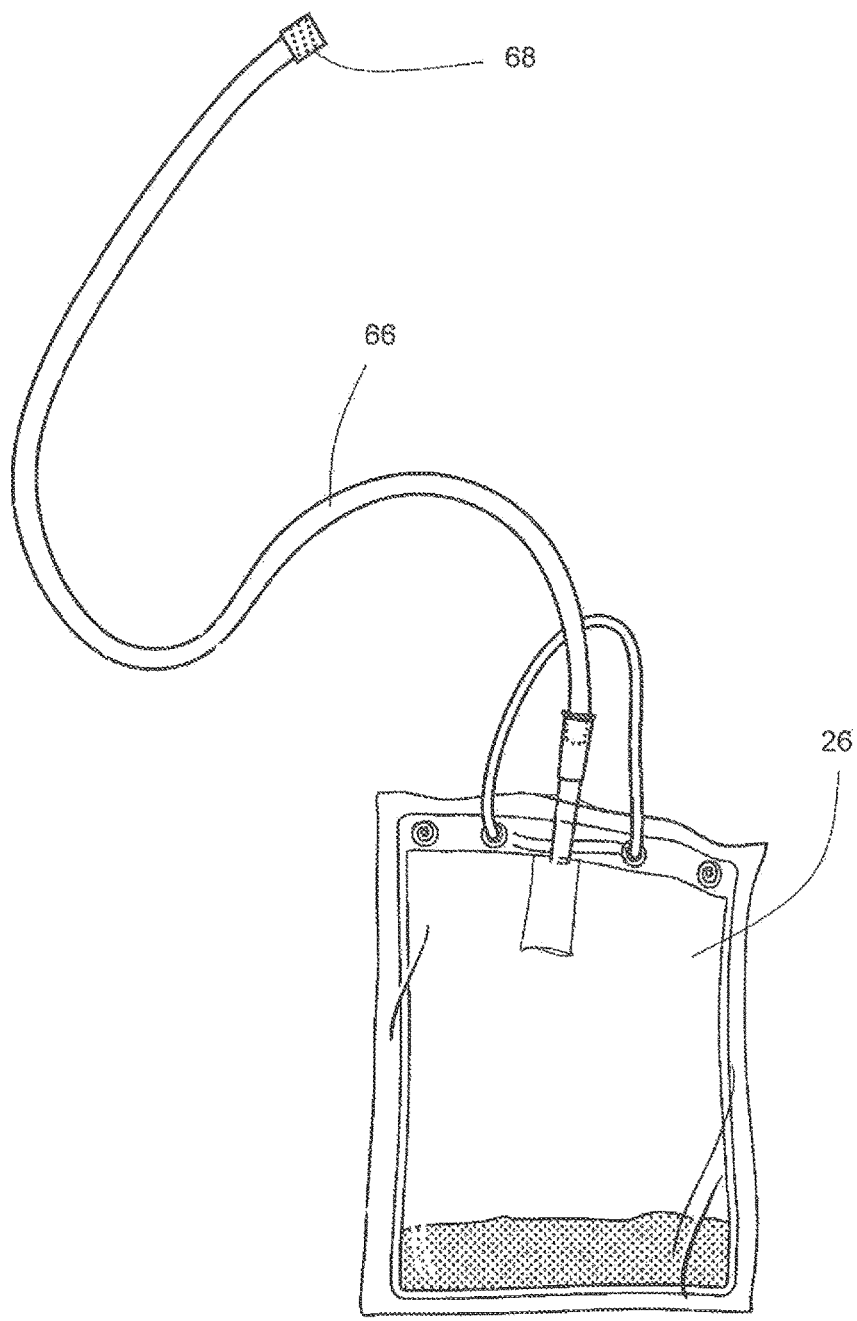
FIG. 12 is a perspective view of an embodiment of a receptacle bag for wound drainage.

FIG. 12 is a perspective view of a drainage system for wound drainage such as drainage of abdominal, chest or thorax-related excess bodily fluids. A catheter is placed in the wound and may lead to a three-way valve (not shown) or 3-way stop cock. The stop cock has three ports (openings connected to each other via an internal tubing). The catheter is inserted into the first port. The second port is a center port with a needleless connector for taking samples of the bodily fluid, and the third port is a connection 68 to a tube 66 leading to a receptacle bag 26 as described above.

The tube 66 is a polymer tube having a first tube end, and a second tube end. The polymer tube has a length between 0.2 m to 2 m, such as 0.5 to 1 m, and, preferably, 0.5 m.

The receptacle bag 26 comprises a receptacle compartment for storing the liquid. It has a receptacle inlet into said receptacle compartment. The receptacle inlet is constituted by a connector having a distal end with respect to the receptacle compartment. The distal end defines a female funnel for receiving the polymer tube, i.e., the first tube end defines a male funnel which is placed in the female funnel. The receptacle bag may contain a volume between 1-2 liters.

The second tube end comprises a male Luer lock fitting 68 for connecting to a female Luer on a stop cock (not shown). The male Luer lock fitting comprises an internal thread.

In the following is a list of reference signs that are used in the detailed description of the invention and the drawings referred to in the detailed description of the invention.

10 Patient
12 Catheter
14 Urinary drainage bag
16 First inlet
18 Collecting compartment
22 Outlet
24 Outlet valve
26 Receptacle bag
28 Receptacle compartment
30 Fluid absorbent powder
32 First tube
34 Connector
36 First end
38 Second end
40 Hanger
42 Closure
44 Closure end
46 Packaging
48 First side
50 Second side
52 First arm
54 Second arm
56 Female part
58 Male part
60 Preform
62 Neck
64 Container part

What is claimed is:

1. A drainage bag system for urinary collection comprising:
    a urinary drainage bag comprising a first inlet and an inlet valve for regulating a flow of urine from a catheter into the urinary drainage bag via the first inlet, an outlet and an outlet valve for regulating a flow of urine out of the urinary drainage bag;
    a receptacle bag for emptying the urinary drainage bag comprising:
        a receptacle compartment for storing urine;
        a connector for providing a connection between the receptacle bag and the urinary drainage bag, the connector providing a second inlet constituting a receptacle inlet to the receptacle compartment when connected to the receptacle bag such that urine can flow into the receptacle compartment; and
        a hanger for hanging the receptacle bag on the urinary drainage bag such that a force of gravity on the receptacle bag tightening the connection, or for carrying the receptacle bag for preventing contamination from the receptacle bag and a closure for closing a passageway in the connector when carrying the receptacle bag.

2. The drainage bag system according to claim 1, wherein the receptacle compartment comprises a fluid absorbent powder for stabilizing urine.

3. The drainage bag system according to claim 1, further comprising a pipe for passing a fluid absorbent powder into the receptacle compartment.

4. The drainage bag system according to claim 1, wherein the receptacle bag is formed by stretch blow molding a preform, further including the connector.

5. The drainage bag system according to claim 1, wherein the receptacle bag comprises a first foil and a second foil, the first foil and the second foil being welded together proximate edges of the first foil and the second foil, and wherein the connector constitutes a separate component.

6. The drainage bag system according to claim 1, wherein the receptacle bag is made from a fibrous pulp material.

7. The drainage bag system according to claim 1, wherein the connector comprises a distal end constituting a female funnel for placement around the outlet such that the outlet is protected from contamination up into the urinary drainage bag.

8. A method for emptying a urinary drainage bag, the method comprising:
providing a urinary drainage bag comprising a first inlet and an inlet valve for regulating a flow of urine from a catheter into the urinary drainage bag via the first inlet, the urinary drainage bag further comprising an outlet and an outlet valve for regulating a flow of urine out of the urinary drainage bag;
providing a receptacle bag for emptying the urinary drainage bag comprising a receptacle compartment for storing urine;
a connector for providing a connection between the receptacle bag and the urinary drainage bag, the connector providing a second inlet constituting a receptacle inlet to the receptacle compartment when connected to the receptacle bag such that urine can flow into the receptacle compartment;
a hanger for hanging the receptacle bag on the urinary drainage bag such that a force of gravity on the receptacle bag tightening the connection, or for carrying the receptacle bag for preventing contamination from the receptacle bag and a closure for closing a passageway in the connector when carrying the receptacle bag; and
connecting the connector to the outlet and opening the outlet valve for providing a flow of urine out of the urinary drainage bag and into the receptacle bag.

9. The method according to claim 8, wherein the receptacle bag is placed at a lower height than a height of the urinary drainage bag such that gravity forces urine from the urinary drainage bag into the receptacle bag.

10. The method according to claim 8, wherein the receptacle bag is placed at a same height as a height of the urinary drainage bag and applying pressure to the urinary drainage bag such that urine is pressed from the urinary drainage bag and into the receptacle bag.

11. A receptacle bag of a foil or sheet material for emptying a urinary drainage bag, comprising a receptacle compartment for storing urine emptied from the urinary drainage bag, and a connector for providing a connection between the receptacle bag and the urinary drainage bag, the connector providing a second inlet constituting a receptacle inlet to the receptacle compartment when connected to the receptacle bag such that urine can flow into the receptacle compartment.

12. The receptacle bag according to claim 11, wherein the receptacle bag is formed by stretch blow molding a preform, further including the connector.

13. The receptacle bag according to claim 11, wherein the receptacle compartment comprises a first foil and a second foil, the first foil and the second foil being welded together proximate edges of the first foil and the second foil, and wherein the connector constitutes a separate component.

14. The receptacle bag according to claim 11, wherein the receptacle bag is made from a fibrous pulp material.

15. A receptacle bag for excess bodily fluids collection such as comprising urinary collection or wound drainage, comprising:
a receptacle compartment configured for storing the excess bodily fluids;
a fluid-absorbent powder contained in the receptacle compartment;
a connector defining a receptacle bag inlet and configured for fluidly coupling a drainage bag outlet or a catheter to the receptacle compartment, so as to permit flow of excess bodily fluids into the receptacle compartment from the drainage bag outlet or the catheter; and
a non-return receptacle valve configured for regulating the flow of excess bodily fluids through the receptacle bag inlet into the receptacle compartment, wherein the non-return receptacle valve is further configured for allowing fluid to flow only into the receptacle compartment and for allowing the fluid-absorbent powder to be introduced through the receptacle bag inlet into the receptacle compartment.

16. The receptacle bag according to claim 15, wherein the receptacle compartment comprises a first foil and a second foil, the first foil and the second foil being welded together proximate edges of the first foil and the second foil, and wherein the connector constitutes a separate component.

17. The receptacle bag according to claim 15, further comprising a tube extending from the connector.

18. The receptacle bag according to claim 17, the tube having a length of up to 2 m.

* * * * *